US011866173B2

United States Patent
Tsukada et al.

(10) Patent No.: US 11,866,173 B2
(45) Date of Patent: Jan. 9, 2024

(54) G TOLERANCE IMPROVEMENT DEVICE AND CONTROL METHOD

(71) Applicant: NIPPON TELEGRAPH AND TELEPHONE CORPORATION, Tokyo (JP)

(72) Inventors: Shingo Tsukada, Atsugi (JP); Hiroshi Nakashima, Atsugi (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 462 days.

(21) Appl. No.: 16/648,216

(22) PCT Filed: Sep. 21, 2018

(86) PCT No.: PCT/JP2018/034966
§ 371 (c)(1),
(2) Date: Mar. 17, 2020

(87) PCT Pub. No.: WO2019/059332
PCT Pub. Date: Mar. 28, 2019

(65) Prior Publication Data
US 2020/0283150 A1 Sep. 10, 2020

(30) Foreign Application Priority Data
Sep. 21, 2017 (JP) .................. 2017-181382

(51) Int. Cl.
*B64D 10/00* (2006.01)
*A61H 7/00* (2006.01)
(Continued)

(52) U.S. Cl.
CPC ............. *B64D 10/00* (2013.01); *A61H 7/001* (2013.01); *A61H 9/0078* (2013.01);
(Continued)

(58) Field of Classification Search
CPC .. B64D 10/00; B64D 2010/002; A61H 7/001; A61H 9/0078; A61H 2201/5058;
(Continued)

(56) References Cited

U.S. PATENT DOCUMENTS 4,534,338 A * 8/1985 Crosbie .................. B64D 10/00
600/19
5,503,157 A * 4/1996 Sramek ................ A61B 5/0535
600/506

(Continued)

FOREIGN PATENT DOCUMENTS

JP H04166498 A 6/1992
JP H04166498 A * 10/1992
JP 2014521427 A 8/2014

OTHER PUBLICATIONS

S. Maruyama et al., Aiming to improve pilot G resistance, The 19th Annual Meeting of the Japanese Society of Pathophysiology, Japanese Society of Pathophysiology, 18(1), pp. 39-41, May 20, 2009.
(Continued)

*Primary Examiner* — Justine R Yu
*Assistant Examiner* — Matthew R Moon
(74) *Attorney, Agent, or Firm* — Harness, Dickey & Pierce, P.L.C.

(57) ABSTRACT

Provided is a G tolerance improvement device provided with: an estimation unit that estimates either or both of a body fluid volume in the head of a user and a change amount of the body fluid volume; and a pressurization unit that applies pressure to the user on the basis of either or both of the body fluid volume and the change amount estimated by the estimation unit.

15 Claims, 6 Drawing Sheets

(51) Int. Cl.
*A61H 9/00* (2006.01)
*A61B 5/0295* (2006.01)
*A61B 5/0537* (2021.01)
*A61B 5/00* (2006.01)

(52) U.S. Cl.
CPC .......... *A61B 5/0295* (2013.01); *A61B 5/0537* (2013.01); *A61B 5/6814* (2013.01); *A61B 5/6822* (2013.01); *A61B 5/6823* (2013.01); *A61H 2201/5058* (2013.01); *A61H 2205/02* (2013.01); *A61H 2205/04* (2013.01); *A61H 2205/083* (2013.01); *A61H 2205/084* (2013.01); *A61H 2205/086* (2013.01); *A61H 2205/088* (2013.01); *B64D 2010/002* (2013.01)

(58) Field of Classification Search
CPC .......... A61H 2205/02; A61H 2205/04; A61H 2205/083; A61H 2205/084; A61H 2205/086; A61H 2205/088; A61H 2201/1409; A61H 2201/1604; A61H 2201/1609; A61H 2201/165; A61H 2201/5084; A61H 2205/06; A61H 2205/10; A61H 2230/655; A61H 1/00; A61B 5/0295; A61B 5/0537; A61B 5/6814; A61B 5/6822; A61B 5/6823; A61B 5/4869

See application file for complete search history.

(56) References Cited

U.S. PATENT DOCUMENTS

| | | | |
|---|---|---|---|
| 2005/0202375 A1* | 9/2005 | Nevo | B64D 10/00 434/59 |
| 2010/0069765 A1* | 3/2010 | Keren | A61B 5/026 600/504 |
| 2011/0282130 A1 | 11/2011 | Krueger | |
| 2014/0194721 A1 | 7/2014 | Pallas Areny et al. | |
| 2017/0367922 A1* | 12/2017 | Pfeiffer | A61H 31/00 |
| 2021/0113214 A1* | 4/2021 | Bhogal | A61B 5/6828 |

OTHER PUBLICATIONS

G-suit, Wikipedia, [online] retrieved on Aug. 23, 2017.
International Search Report (in English and Japanese) issued in International Application PCT/JP2018/034966, dated Nov. 27, 2018; ISA/JP.
Japanese Office Action from counterpart JP2019543722, dated Jun. 9, 2020.

* cited by examiner

US 11,866,173 B2

G TOLERANCE IMPROVEMENT DEVICE AND CONTROL METHOD

CROSS-REFERENCE TO RELATED APPLICATIONS

This application is a 371 National Phase of International Application No. PCT/JP2018/034966, filed on Sep. 21, 2018, which claims priority to Japanese Application No. 2017-181382, filed on Sep. 21, 2017. The entire disclosures of the above applications are incorporated herein by reference.

TECHNICAL FIELD

The present invention relates to a G tolerance improvement device and a control method thereof.

BACKGROUND ART

Conventionally, airplane pilots sometimes experience abnormal conditions such as decreased visual acuity, loss of consciousness, and central nervous system disorders during airplane turns. These abnormal states (hereinafter referred to as "hypoxic brain conditions") are caused by the fact that centrifugal acceleration exceeding an allowable amount caused by the turning of an airplane reduces venous return, leading to sufficient oxygen not being supplied to the brain. Therefore, in order to suppress the occurrence of a hypoxic brain state, a device (hereinafter referred to as a "G tolerance improvement device") that increases the pilot's resistance to centrifugal acceleration (hereinafter referred to as "G tolerance") has been used. The G tolerance improvement device is a device including clothing that increases G tolerance, such as a suit that increases G tolerance of the lower body, a vest that increases G tolerance of the upper body, and a helmet that increases G tolerance of the head. In particular, a suit that increases G tolerance is called a G suit. The G tolerance improvement device may also be, for example, a COMBAT EDGE (Combined Advanced Technology Enhanced Design G Ensemble). The airplane may for example be a fighter.

A conventional G tolerance improvement device suppresses the occurrence of a hypoxic brain state by sending compressed air into clothing and compressing the pilot. Specifically, for example, the G suit of the G tolerance improvement device has a structure like a trouser-shaped floating ring or life jacket, and is connected to a connector in the cockpit by a hose when boarding. The G tolerance improvement device is provided with an accelerometer, and when the acceleration measured by the accelerometer exceeds a predetermined magnitude, compressed air is fed into the G suit. Such a G tolerance improvement device compresses the lower body of the pilot by sending compressed air into the G suit, thereby lessening a lowering of the blood and so suppressing the occurrence of decreased visual acuity, loss of consciousness, and central nervous system disorders.

The G tolerance improvement device provides the same function as such a G suit in clothing such as a vest and a helmet. In this way, the G tolerance improvement device exerts pressure on the lower body, upper body, and head, thereby suppressing the occurrence of a hypoxic brain state.

CITATION LIST

[Non-Patent Document]
Non-patent Document 1: Maruyama S., Takahata T., Shoji I., Manabe T., Nishida Y., "Aiming to improve pilot G tolerance" The 19th Annual Meeting of Society of Pathophysiology, Japanese journal of pathophysiology 18(1), 39-41, 2009-05-20
Non-patent Document 2: "G-suit." Wikipedia: Japanese-language version. Retrieved Aug. 23, 2017, from https://ja.wikipedia.org/wiki/%E8%80%90G%E3%82%B9%E3%83%BC%E3%83%84

SUMMARY OF THE INVENTION

Problems to be Solved by the Invention

However, a conventional G tolerance improvement device may not recognize the pilot's state. For this reason, there was a problem that pressure could not be applied appropriately to the pilot.

In view of the above circumstances, the object of the present invention is to provide a technique capable of appropriately applying pressure to a user such as a pilot.

Means for Solving the Problems

One aspect of the present invention is a G tolerance improvement device includes: an estimation unit that estimates either or both of a body fluid volume in the head of a user and a change amount of the body fluid volume; and a pressurization unit that applies pressure to the user based on either or both of the body fluid volume and the change amount estimated by the estimation unit.

One aspect of the present invention is the aforementioned G tolerance improvement device, further provided with: a first electrode unit provided with a first electrode that makes contact with the head of the user; and a second electrode unit provided with a second electrode that makes contact with the user at a location different from the location where the first electrode makes contact, in which the estimation unit estimates either or both of the body fluid volume and the change amount based on the impedance between the first electrode unit and the second electrode unit.

One aspect of the present invention is the aforementioned G tolerance improvement device, in which either one or both of the first electrode unit and the second electrode unit are provided with two or more electrodes.

One aspect of the present invention is the aforementioned G tolerance improvement device, in which the head with which the first electrode makes contact is either one or both of the crown or temple region of the head of the user.

One aspect of the present invention is the aforementioned G tolerance improvement device, in which the location that the second electrode makes contact with is any one or all of the head, neck, chest, abdomen, waist, and buttocks of the user.

One aspect of the present invention is the aforementioned G tolerance improvement device, in which the body fluid volume estimated by the estimation unit is the body fluid volume in the cranium of the user.

One aspect of the present invention is the aforementioned G tolerance improvement device, in which the change amount is the venous return.

One aspect of the present invention is the aforementioned G tolerance improvement device, in which the estimation unit estimates the body fluid volume, and the pressurization unit applies pressure to the user when the body fluid volume is equal to or less than a first threshold value.

One aspect of the present invention is the aforementioned G tolerance improvement device, in which the estimation unit further estimates the change amount, and the pressurization unit applies pressure to the user when the change amount exceeds a second threshold even when the body fluid volume is greater than the first threshold value.

One aspect of the present invention is the aforementioned G tolerance improvement device, in which the estimation unit estimates the change amount, and the pressurization unit applies pressure to the user when the change amount exceeds a second threshold value.

One aspect of the present invention is the aforementioned G tolerance improvement device, in which the pressurization unit applies pressure to any of the neck, armpits, lower limbs, abdomen, waist, chest, and upper limbs of the user.

One aspect of the present invention is the aforementioned G tolerance improvement device, in which the pressurization unit reduces the pressurization amount when the period of applying pressure reaches a predetermined period.

One aspect of the present invention is the aforementioned G tolerance improvement device, in which the pressurization unit reduces the pressurization amount when the body fluid volume is equal to or greater than a third threshold value.

One aspect of the present invention is the aforementioned G tolerance improvement device, further provided with an accelerometer that measures acceleration applied to the user, in which the estimation unit estimates either or both of the body fluid volume or the change amount when the acceleration is greater than a fourth threshold value.

One aspect of the present invention is a control method including: estimating either of a body fluid volume in the head of a user or a change amount of the body fluid volume, and applying pressure to the user on the basis of either or both of the estimated body fluid volume and the change amount.

Effects of the Invention

With the present invention it is possible to appropriately apply pressure to a user.

EMBODIMENTS FOR CARRYING OUT THE INVENTION

Figure 1:
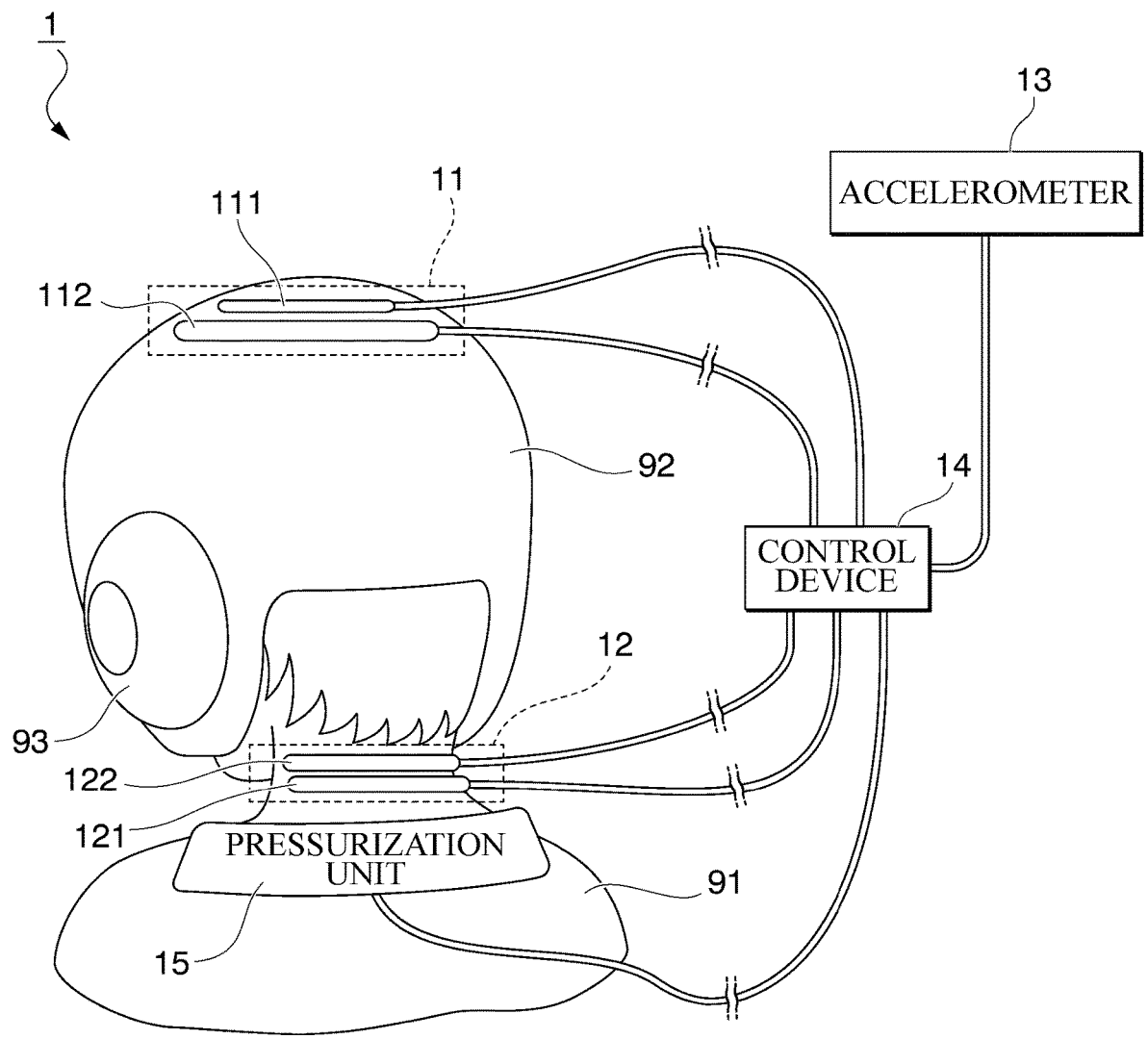
FIG. 1 is a drawing showing an example of use of a G tolerance improvement device 1 according to the embodiment.

FIG. 1 is a drawing showing an example of use of a G tolerance improvement device 1 of the embodiment. The G tolerance improvement device 1 of the embodiment applies a current or voltage to the head of a user 91 via an electrode to acquire the impedance of the head and thereby estimates the body fluid volume in the cranium and a change amount thereof. The G tolerance improvement device 1 of the embodiment applies a pressure based on the estimated body fluid volume and change amount thereof to the neck of the user 91 to suppress a lowering of the blood, and maintains the body fluid volume of the head of the user 91 at an appropriate amount. Blood volume is an amount having a high correlation to the body fluid volume in the cranium. Therefore, the body fluid volume in the cranium may be, for example, the amount of blood in the cranium.

The G tolerance improvement device 1 according to the embodiment is provided with a first electrode unit 11, a second electrode unit 12, an accelerometer 13, a control device 14, and a pressurization unit 15.

The first electrode unit 11 is provided with an electrode that makes contact with the head of the user 91. More specifically, the first electrode unit 11 is provided with a first application electrode 111 and a first measurement electrode 112. The first measurement electrode 112 is located between the first application electrode 111 and a second electrode unit 12. Provided the first application electrode 111 and the first measurement electrode 112 are in contact with the head of the user 91, contact may be made by any method. For example, the first application electrode 111 and the first measurement electrode 112 may be in contact with the head of the user 91 wearing a helmet 92 by being attached to the crown of the helmet 92. Alternatively, the first application electrode 111 and the first measurement electrode 112 may be attached to the helmet 92 and an ear muff 93 of a headphone to make contact with a temple region of the user 91. By the helmet 92 and the ear muff 93 of the headphone covering a temple region of the user 91, the first application electrode 111 and the first measurement electrode 112 make contact with a temple region of the user 91. In addition, for example, by being attached to the crown of a face mask, the first application electrode 111 and the first measurement electrode 112 may make contact with the head of the user 91 wearing the face mask. The helmet 92 is an impact absorbing protector used in an environment where impacts are received. The helmet 92 is not only provided so that the first application electrode 111 and the first measurement electrode 112 are in contact with the user 91, but is also a head protecting member that protects the user 91 in an environment where impacts are received.

In addition, the user 91 may bring the first application electrode 111 and the first measurement electrode 112 into contact with his body by wearing a hood-like cloth to which the first application electrode 111 and the first measurement electrode 112 are attached, and then wear the helmet 92 thereon.

A voltage is applied between the first application electrode 111 and the second electrode unit 12 in order to measure the impedance of the head of the user 91. Therefore, when the first measurement electrode 112 is located between the first application electrode 111 and the second electrode unit 12, the impedance of the head is measured with high accuracy compared to the case where the first measurement electrode 112 is not located between the first application electrode 111 and the second electrode unit 12.

Note that the first measurement electrode 112 is located between the first application electrode 111 and the second electrode unit 12 means the following. A curve connecting the center point of the first application electrode 111 and the center point of the second electrode unit 12 and parallel to the surface of the head of the user 91 is assumed to be an H line. Being located between the first application electrode 111 and the second electrode unit 12 means that a part of the first measurement electrode 112 is located on the H line sandwiched between the center point of the first application electrode 111 and the center point of the second electrode unit 12. That is, the first measurement electrode 112 may be located at a position below the position shown in FIG. 1.

However, the first measurement electrode 112 is not necessarily located between the first application electrode 111 and the second electrode unit 12, and may be located at any position in consideration of the impedance measurement accuracy provided the impedance of the head can be measured.

In the G tolerance improvement device 1 of the present embodiment, it is desirable that the first measurement electrode 112 is located between the first application electrode 111 and the second electrode unit 12.

The second electrode unit 12 is provided with an electrode that contacts the neck of the user 91. More specifically, the second electrode unit 12 is provided with a second application electrode 121 and a second measurement electrode 122. The second measurement electrode 122 may be located between the second application electrode 121 and the first electrode unit 11. The second electrode unit 12 does not necessarily need to contact the neck, and may make contact with any location provided the location is one at which the impedance of the head can be measured. For example, the second electrode unit 12 may be attached to the chest, abdomen, waist, or buttocks of the user 91. Further, the second electrode unit 12 may be attached to any place on the head that differs from the first electrode unit.

A voltage is applied between the second application electrode 121 and the first electrode unit 11 in order to measure the impedance of the head of the user 91. Therefore, when the second measurement electrode 122 is located between the second application electrode 121 and the first electrode unit 11, the impedance of the head is measured with high accuracy compared with the case where the second measurement electrode 122 is not located between the second application electrode 121 and the first electrode unit 11.

Note that the second measurement electrode 122 being located between the second application electrode 121 and the first electrode unit 11 means the following. A curve connecting the center point of the second application electrode 121 and the center point of the first electrode unit 11 and parallel to the surface of the head of the user 91 is assumed to be an I line. Being located between the second application electrode 121 and the first electrode unit 11 means that a part of the second measurement electrode 122 is located on the I line sandwiched between the center point of the second application electrode 121 and the center point of the first electrode unit 11. That is, the second measurement electrode 122 may located at a position above the position shown in FIG. 1.

However, the second measurement electrode 122 is not necessarily located between the second application electrode 121 and the first electrode unit 11, and may be located at any position in consideration of the impedance measurement accuracy provided the position is one at which the impedance of the head can be measured.

In the G tolerance improvement device 1 of the present embodiment, it is desirable that the second measurement electrode 122 is located between the second application electrode 121 and the first electrode unit 11.

The accelerometer 13 measures the acceleration applied thereto and outputs a signal indicating the magnitude of the acceleration (hereinafter referred to as "acceleration signal"). The accelerometer 13 may be located at any position as long as the accelerometer 13 is installed at a location subjected to substantially the same acceleration as that applied to the user 91.

For example, the accelerometer 13 may be attached to the helmet 92 worn by the user 91, or may be attached to an object that is subjected to substantially the same acceleration as the user 91, such as a seat of an airplane on which the user 91 has boarded.

The control device 14 is electrically connected to the first electrode unit 11 and the second electrode unit 12 and controls the first electrode unit 11 and the second electrode unit 12. On the basis of the current flowing through the first electrode unit 11 and the second electrode unit 12 and the acceleration signal output from the accelerometer 13, the control device 14 performs control so that the pressurization unit 15 applies pressure of a predetermined level determined in advance at a location in contact with the pressurization unit 15.

The pressurization unit 15 makes contact with the neck of the user 91 and applies pressure to the neck of the user 91 under the control of the control device 14. The region to which pressure is applied is not limited to the example of FIG. 1. The pressurization unit 15 may apply pressure to other regions instead of the neck or in addition to the neck. Other regions are, for example, the armpits, the lower limbs, the abdomen, the waist, the chest, the upper limbs, and the like. The lower limbs, abdomen, waist, chest, and upper limbs may be pressurized with, for example, a G suit. The region to which pressure is applied may be any of the neck, armpits, lower limbs, abdomen, waist, chest, and upper limbs, or a combination thereof.

By the pressurization unit 15 applying pressure to the neck of the user 91 and the like, a decrease in the body fluid volume in the cranium of the user 91 is suppressed, and so the occurrence of an abnormal state in the user 91 such as decreased visual acuity, loss of consciousness, or a central nervous system disorder is suppressed. The pressurization unit 15 may be any unit that applies pressure to the neck of the user 91 and the like. For example, the pressurization unit 15 may be an airbag. The pressurization unit 15 may pressurize the entire circumference of the neck uniformly, may selectively pressurize the front surface of the neck (front neck portion), and may selectively pressurize around the jugular vein.

Figure 2:
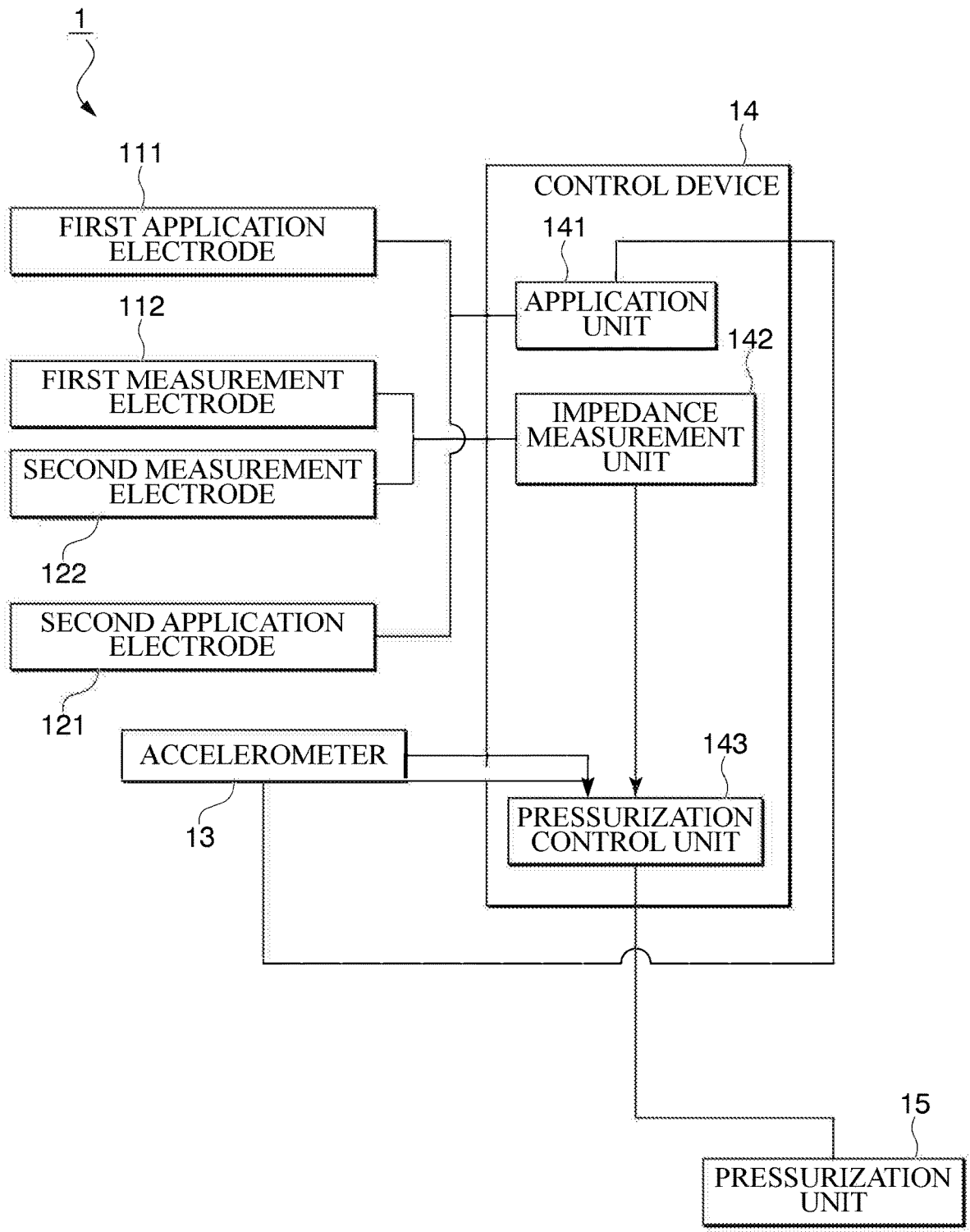
FIG. 2 is a diagram showing a specific example of the configuration of the G tolerance improvement device 1 of the embodiment.

FIG. 2 is a diagram showing a specific example of the configuration of the G tolerance improvement device 1 according to the embodiment.

The control device 14 is provided with an application unit 141, an impedance measurement unit 142, and a pressurization control unit 143.

The application unit 141 applies a voltage between the first application electrode 111 and the second application electrode 121. The application unit 141 may be any device as long as a voltage can be applied between the first application electrode 111 and the second application electrode 121. For example, the application unit 141 may be a voltage source.

The impedance measurement unit 142 measures the impedance between the first measurement electrode 112 and the second measurement electrode 122 by acquiring the current flowing through the first measurement electrode 112 and the second measurement electrode 122.

The pressurization control unit 143 controls the pressure applied by the pressurization unit 15 to the user 91 on the basis of the acceleration signal output from the accelerometer 13 and the impedance measured by the impedance measurement unit 142. More specifically, the pressurization control unit 143 estimates the body fluid volume in the cranium of the user 91 and a change amount of the body fluid volume per unit time based on the impedance measured by the impedance measurement unit 142. The pressurization control unit 143 controls whether or not the pressurization unit 15 applies pressure to the user 91 on the basis of the estimated body fluid volume and the change amount of the body fluid volume per unit time. The change amount of the body fluid volume may be, for example, the venous return.

Note that when the body fluid volume in the cranium is small, since it is difficult for current to flow through the cranium, the impedance of the head becomes larger compared to the case of the body fluid volume being large. Therefore, for example, the pressurization control unit 143 estimates the body fluid volume in the cranium to be small when the impedance measured by the impedance measurement unit 142 is larger than a predetermined impedance.

Figure 3:
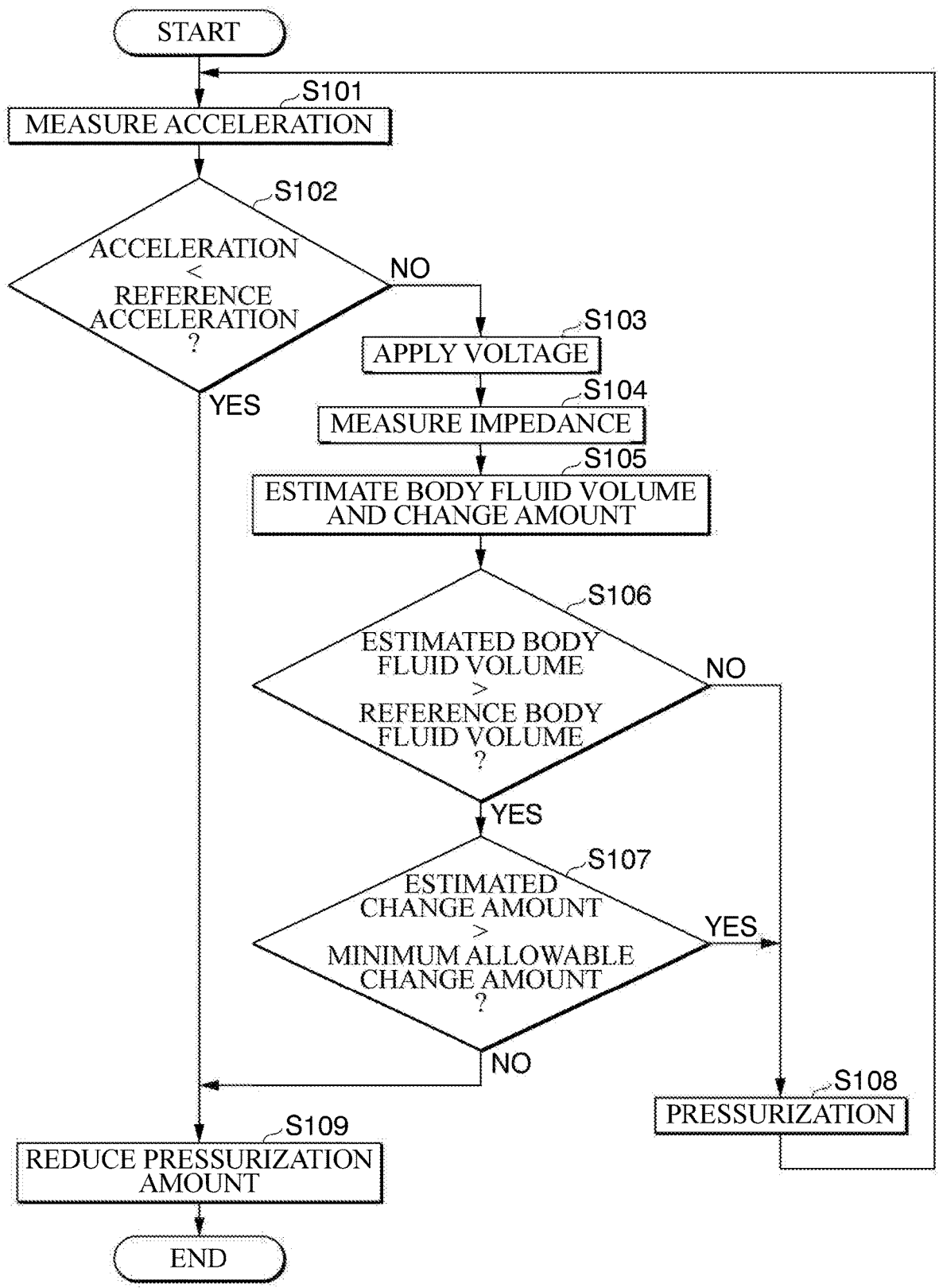
FIG. 3 is a flowchart showing a specific processing flow in which the G tolerance improvement device 1 according to the embodiment applies pressure to the user's neck.

FIG. 3 is a flowchart illustrating a specific processing flow in which the G tolerance improvement device 1 according to the embodiment pressurizes the user's neck.

The accelerometer 13 measures the acceleration and outputs an acceleration signal (Step S101). The pressurization control unit 143 acquires the acceleration signal and determines whether or not the acceleration signal is less than a predetermined value (hereinafter referred to as "reference acceleration") (Step S102). When the acceleration is equal to or greater than the reference acceleration (Step S102: No), the application unit 141 applies a voltage between the first application electrode 111 and the second application electrode 121 (Step S103). The impedance measurement unit 142 acquires a current flowing through the first measurement electrode 112 and the second measurement electrode 122. The current flowing through the first measurement electrode 112 and the second measurement electrode 122 is a current generated by the voltage applied by the application unit 141. The impedance measurement unit 142 measures the impedance between the first measurement electrode 112 and the second measurement electrode 122 on the basis of the current value of the acquired current and the voltage applied by the application unit 141 (Step S104).

The pressurization control unit 143 acquires the impedance measured by the impedance measurement unit 142, and estimates the body fluid volume in the cranium of the user 91 and the change amount per unit time (Step S105). The pressurization control unit 143 determines whether or not the body fluid volume that has been estimated (hereinafter referred to as "estimated body fluid volume") is greater than a predetermined body fluid volume (hereinafter referred to as "reference body fluid volume") (Step S106).

When the estimated body fluid volume is greater than the reference body fluid volume (Step S106: Yes), the pressurization control unit 143 determines whether or not the estimated change amount in the body fluid volume (hereinafter referred to as "estimated change amount") is greater than a predetermined value (hereinafter referred to as "minimum allowable change amount") (Step S107).

The estimated change amount may indicate a decrease amount or an increase amount. When the estimated change amount indicates a decrease amount, the minimum allowable change amount is an amount indicating that, when the estimated change amount is larger than the minimum allowable change amount, there is a high risk of decreased visual acuity, loss of consciousness, a central nervous system disorder, or the like occurring in the user 91. When the estimated change amount indicates an increase amount, the minimum allowable change amount is an amount indicating that, when the estimated change amount is larger than the minimum allowable change amount, there is a high risk of an increase in intracranial pressure, brain damage, or the like occurring in the user 91. When inverse G occurs, the body fluid volume may increase rapidly. Reverse G indicates upward G.

When the estimated change amount is larger than the minimum allowable change amount (Step S107: Yes), the pressurization control unit 143 controls the pressurization unit 15 to apply pressure to the user 91 (Step S108).

More specifically, when downward G is applied and the estimated change amount indicates a decrease amount, the pressurization control unit 143 applies pressure to the user 91. Alternatively, when pressure is already being applied, the pressurization control unit 143 increases the pressurization amount. When upward G (reverse G) is applied and the estimated change amount indicates an increase amount, the pressurization control unit 143 applies pressure to the user 91. Alternatively, when pressure is already being applied, the pressurization control unit 143 increases the pressurization amount.

In this way, even if the estimated body fluid volume is larger than the reference body fluid volume, the pressurization control unit 143 increases the pressurization amount applied to the user 91 when the estimated change amount is larger than the minimum allowable change amount. This suppresses the movement of body fluid to the head. Based on the change amount of the body fluid volume, the pressurization amount can be appropriately controlled without being affected by individual differences in body fluid volume.

It should be noted that the pressurization unit 15 may adjust the region to which pressure is applied and the manner in which the pressure is applied depending on whether the estimated change amount indicates a decrease amount or an increase amount. For example, when reverse G is applied and the estimated change amount indicates an increase amount, the pressurization unit 15 applies pressure to both sides of the neck. In this case, the pressurization unit 15 may apply pressure to both sides of the neck and reduce the pressurization amount to the lower limbs and the abdomen. Thereby, movement of bodily fluid can be appropriately suppressed.

On the other hand, in Step S106, when the estimated body fluid volume is equal to or less than the reference body fluid volume (Step S106: No), the pressurization control unit 143 controls the pressurization unit 15 to apply pressure to the user 91 (Step S108).

In this way, the pressurization control unit 143 applies pressure to the user 91 when the estimated body fluid volume is equal to or less than the reference body fluid volume or when the estimated change amount is larger than the minimum allowable change amount.

On the other hand, when the estimated change amount is equal to or less than the minimum allowable change amount in Step S107 (Step S107: No), the pressurization control unit 143 controls the pressurization unit 15 so that the pressurization unit 15 lowers the pressure applied to the user 91 (Step S109). In addition, when the pressurization unit 15 does not apply pressure to the user 91, the pressure of the pressurization unit 15 does not become lower than that.

In this way, when pressure is applied to the user 91, the pressurization control unit 143 decreases the pressurization amount when the estimated change amount is less than or equal to the minimum allowable change amount. Alternatively, when no pressure is applied to the user 91, the pressurization control unit 143 does not apply pressure to the user 91 while the estimated change amount is less than or equal to the minimum allowable change amount.

On the other hand, when the acceleration is smaller than the reference acceleration in Step S102 (Step S102: Yes), the pressurization control unit 143 controls the pressurization unit 15 to reduce the pressure applied to the user 91 by the pressurization unit 15 (Step S109). In addition, when the pressurization unit 15 does not apply pressure to the user 91, the pressure of the pressurization unit 15 does not become lower than that.

In this way, when the acceleration is equal to or greater than the reference acceleration, the pressurization control unit 143 applies pressure to the user 91 in accordance with the estimated body fluid volume and change amount. Accordingly, it is possible to suppress the application of pressure to the user 91 when the acceleration is less than the reference acceleration. Further, the pressurization control unit 143 can reduce the processing load when the acceleration is less than the reference acceleration.

If pressure is applied from the pressurization unit 15 to the neck continuously for a long time, excessive body fluid builds up in the head and neck, leading to the possibility of the user 91 entering a dangerous state. For this reason, the G tolerance improvement device 1 is further provided with a timer 144 in addition to the functional parts of FIG. 3. It is desirable that the G tolerance improvement device 1 be provided with a safety mechanism (hereinafter referred to as a "first safety mechanism") that automatically reduces the pressurization amount by the pressurizing unit 14 after a certain time (hereinafter referred to as a "limit time") has elapsed from the start of pressurization according to the timer. Further, it is desirable that the G tolerance improvement device 1 be provided with a safety mechanism (hereinafter referred to as a "second safety mechanism") that quickly decreases the pressurization amount when excessive buildup of body fluid is detected on the basis of the impedance value. Thereby, the possibility that the user 91 will be in the above dangerous state can be reduced. The excessive buildup of body fluid means that body fluid exceeding a predetermined body fluid volume is built up in the skull (hereinafter referred to as "allowable body fluid volume").

Figure 4:
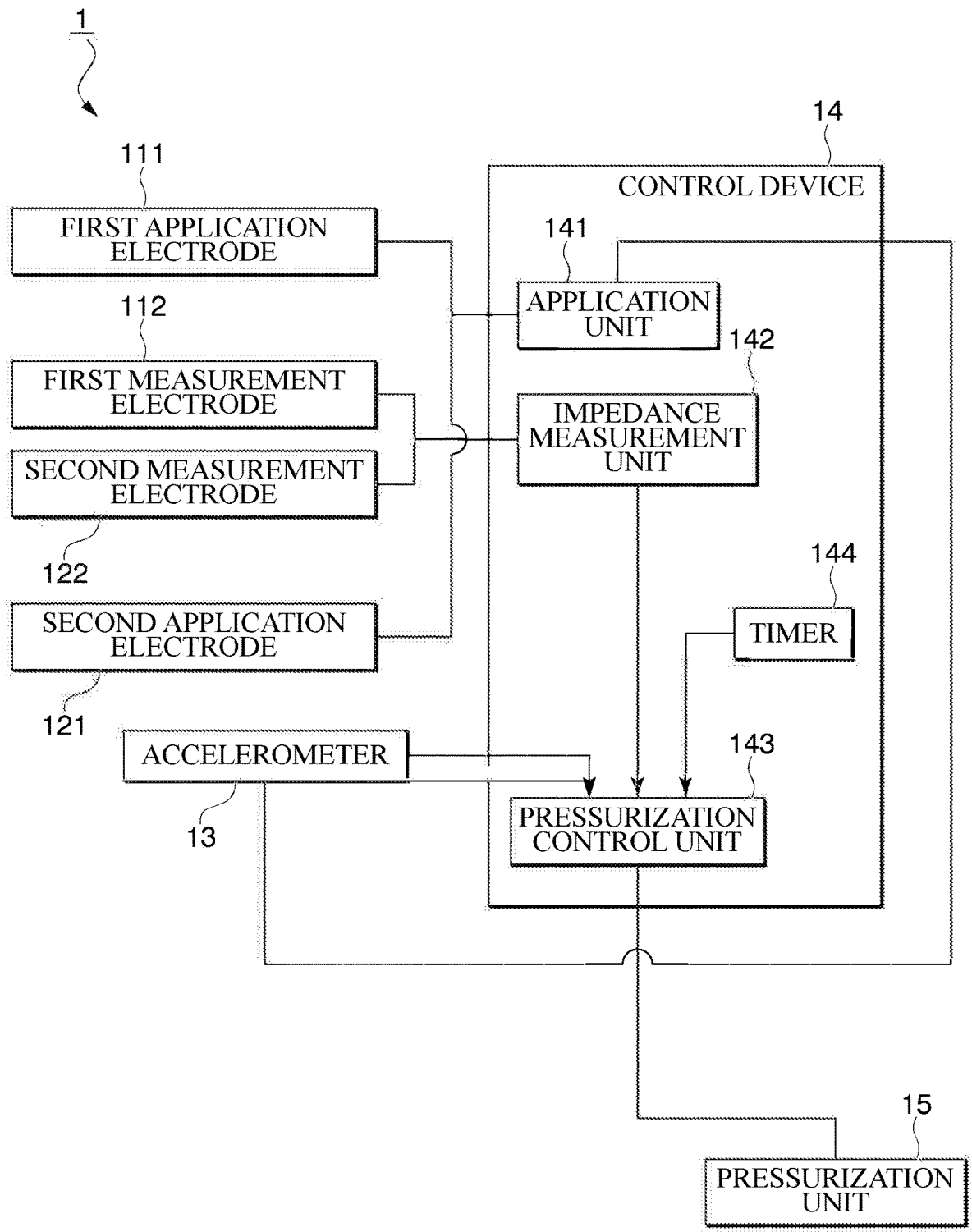
FIG. 4 is a diagram illustrating a specific example of a functional configuration when the G tolerance improvement device 1 according to the embodiment is provided with a safety mechanism 1.

FIG. 4 is a diagram illustrating a specific example of a functional configuration when the G tolerance improvement device 1 of the embodiment is provided with the safety mechanism 1.

The G tolerance improvement device 1 provided with the safety mechanism 1 is provided with a timer 144 in addition to the functional units shown in FIG. 2. The timer 144 measures the time from the time origin, with the time at which the G tolerance improvement device 1 started applying pressure to the user 91 serving as the time origin. The timer 144 outputs the measured time to the pressurization control unit 143. For example, the timer 144 measures the time from the time origin, with the time at which the pressurization control unit 143 started controlling the pressurization unit 15 being the time origin.

Figure 5:
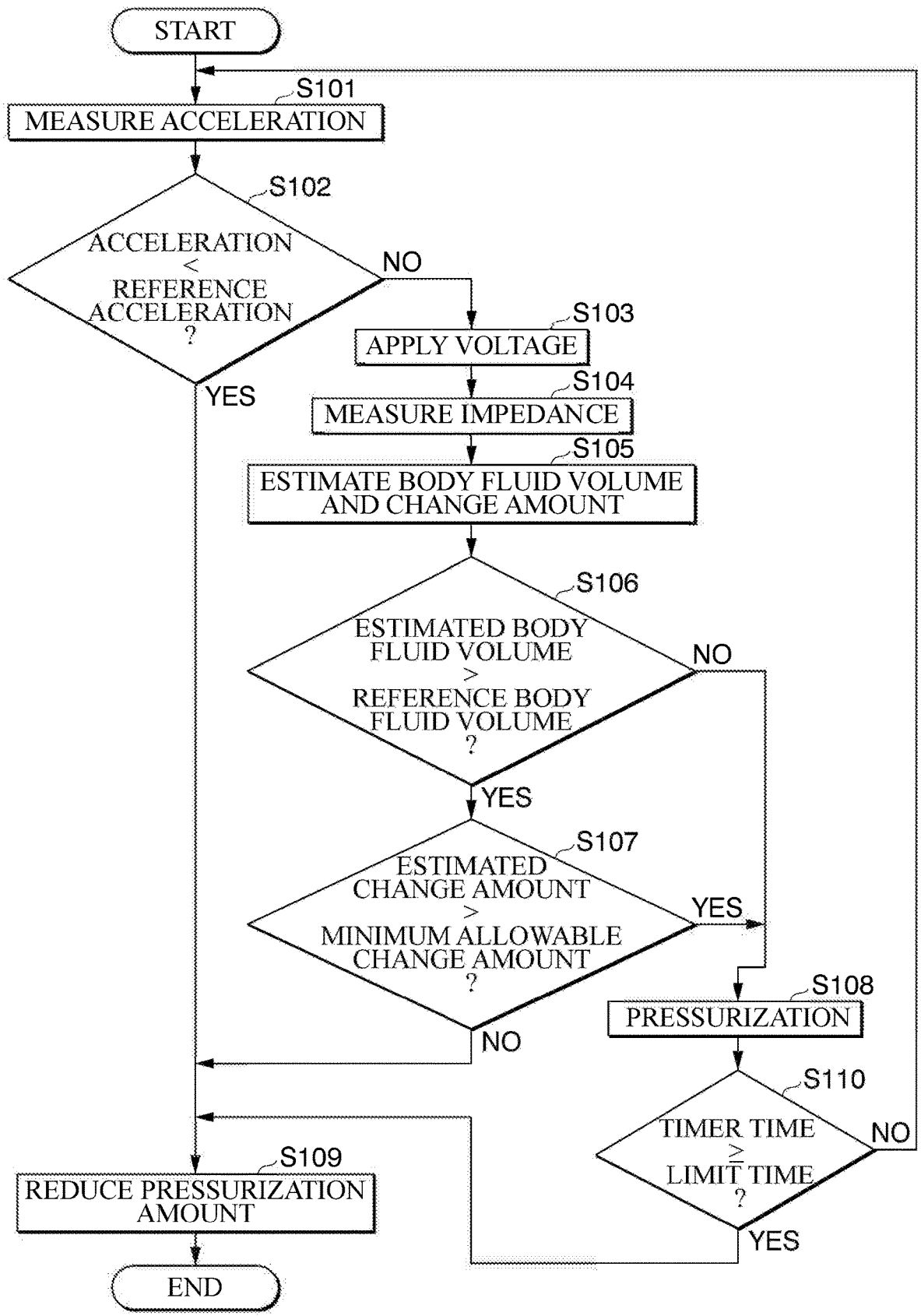
FIG. 5 is a flowchart showing a specific processing flow in which the G tolerance improvement device 1 of the embodiment is provided with the first safety mechanism and pressurizes the user's neck.

FIG. 5 is a flowchart showing a specific processing flow of applying pressure to the user's neck when the G tolerance improvement device 1 of the embodiment is provided with the first safety mechanism. The flowchart of FIG. 5 differs from the flowchart of FIG. 3 on the point of the process of Step S110 being provided immediately after the process of Step S108 in the flowchart of FIG. 3. It should be noted that in the processing of FIG. 5, the same processes as those in FIG. 3 are denoted by the same reference numerals, with descriptions thereof being omitted.

In Step 108, after the pressurization control unit 143 controls the pressurization unit 15 to apply pressure to the user 91, the pressurization control unit 143 acquires the time measured by the timer 144 (hereinafter referred to as "timer time"). The pressurization control unit 143 determines whether or not the timer time is equal to or longer than the limit time (Step S110). When the timer time is equal to or longer than the limit time (Step S110: Yes), the pressurization control unit 143 controls the pressurization unit 15 to reduce the pressure applied to the user 91 by the pressurization unit 15 (Step S109). On the other hand, when the timer time is shorter than the limit time (Step S110: No), the processing of the G tolerance improvement device 1 returns to the process of Step S101.

Figure 6:
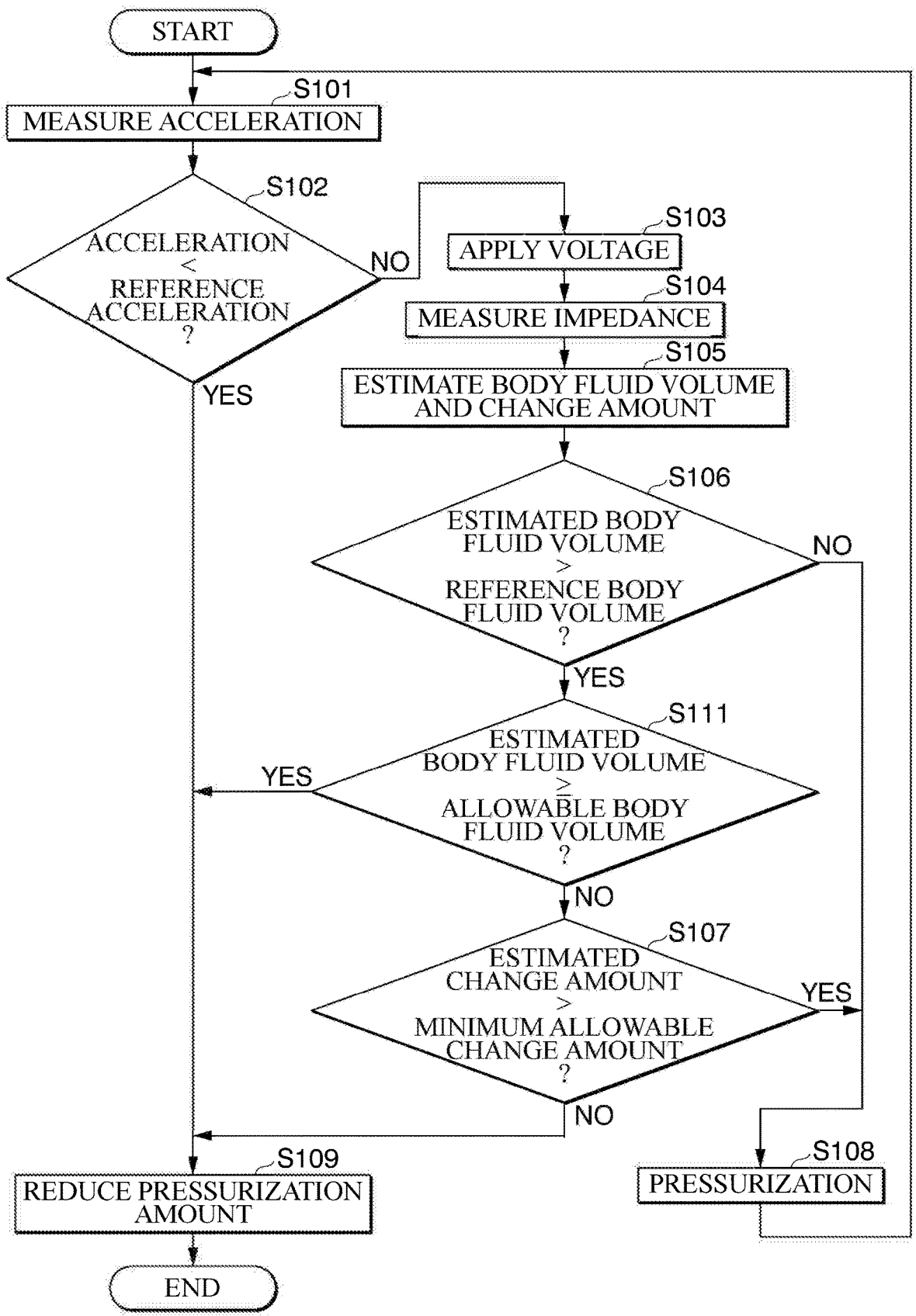
FIG. 6 is a flowchart showing a specific processing flow in which the G tolerance improvement device 1 of the embodiment is provided with a second safety mechanism and pressurizes the user's neck.

FIG. 6 is a flowchart showing a specific processing flow of applying pressure to the user's neck when the G tolerance improvement device 1 of the embodiment is provided with the second safety mechanism. The flowchart of FIG. 6 differs from the flowchart of FIG. 3 on the point of the process of Step S111 being provided between the process of Step S106 and the process of Step S107 in the flowchart of FIG. 3. It should be noted that in the processing of FIG. 6, the same processes as those in FIG. 3 are denoted by the same reference numerals, with descriptions thereof being omitted.

When it is determined in Step S106 that the estimated body fluid volume is greater than the reference body fluid volume (Step S106: Yes), the pressurization control unit 143 determines whether or not the estimated body fluid volume is equal to or greater than the allowable body fluid volume (Step S111). As described above, the allowable body fluid volume is a limit amount when body fluid is excessively built up in the cranium. When downward G is applied and the estimated body fluid volume is equal to or greater than the allowable body fluid volume (Step S111: Yes), the pressurization control unit 143 controls the pressurization unit 15 to lower the pressure applied by the pressurization unit 15 to the user 91 (Step S109). In this way, it is possible to achieve a reduction in the body fluid by detecting that an excessive buildup of body fluid in the cranium has been detected and reducing the pressurization amount. On the other hand, when the estimated body fluid volume is a value smaller than the allowable body fluid volume (Step S111: No), the G tolerance improvement device 1 performs the process of Step S107.

The G tolerance improvement device 1 of the embodiment configured as described above is provided with the pressurization unit 15 in contact with the user's neck and the impedance measurement unit 142 that measures the impedance of the head of the user 91. The G tolerance improvement device 1 is further provided with the pressurization control unit 143 that estimates the body fluid volume in the cranium of the user 91 and the change amount per unit time on the basis of the measured impedance, and controls the pressurization unit 15 on the basis of the estimated values. For this reason, it is possible to apply pressure to a pilot according to the physical condition of each pilot.

(Modification)

The G tolerance improvement device 1 need not necessarily have the second electrode unit 12 in contact with the neck, and may have the second electrode unit 12 in contact with the abdomen or waist.

The first electrode unit 11 of the G tolerance improvement device 1 need not necessarily be provided with two electrodes, and may also be one electrode having the same function as the first application electrode 111 and the first measurement electrode 112. In addition, the second electrode unit 12 of the G tolerance improvement device 1 need not necessarily be provided with two electrodes, and may also be one electrode having the same function as the second application electrode 121 and the second measurement electrode 122.

Furthermore, the first electrode unit 11 of the G tolerance improvement device 1 need not necessarily be provided with two electrodes, and may be provided with three or more.

Furthermore, the second electrode unit 12 of the G tolerance improvement device 1 need not necessarily be provided with two electrodes, and may be provided with three or more.

Although the impedance measurement method of the embodiment is a so-called four-terminal method, the impedance measurement method in the case where each of the first electrode unit 11 and the second electrode unit 12 is provided with only one electrode is a so-called two-terminal method.

In addition, the G tolerance improvement device 1 need not necessarily be provided with two electrode units, and may be provided with one or three or more.

Note that the application unit 141, the impedance measurement unit 142, and the pressurization control unit 143 need not necessarily be mounted as a single housing, and some or all of the function units may be individually mounted.

Note that the application of the voltage in Step S103 of FIG. 3 need not necessarily be performed in Step S103, and may be performed any time provided the application is before the impedance measurement in Step S104.

Note that a voltage need not necessarily be applied between the first measurement electrode 112 and the second measurement electrode 122, and a current may be applied. Further, the impedance measurement unit 142 need not necessarily measure the impedance by acquiring the current flowing through the first measurement electrode 112 and the second measurement electrode 122. The impedance measurement unit 142 may measure the impedance by acquiring the voltage flowing through the first measurement electrode 112 and the second measurement electrode 122.

The method of estimating the body fluid volume by the G tolerance improvement device 1 is not necessarily a method based on impedance, and may be any method provided the method is capable of estimating the body fluid volume of the head of the user 91. The body fluid volume of the head of the user 91 may be estimated by, for example, a change in reflectance or transmittance of electromagnetic waves such as infrared rays irradiated on the head of the user 91.

In the estimation method using electromagnetic waves such as infrared rays, the G tolerance improvement device 1 may be provided with a light receiving element instead of the first electrode unit 11, the second electrode unit 12, and the impedance measurement unit 142. In the estimation method using electromagnetic waves such as infrared rays, the G tolerance improvement device 1 may be provided with a light source that emits electromagnetic waves such as infrared rays instead of the application unit 141. Moreover, in the estimation method using electromagnetic waves such as infrared rays, the G tolerance improvement device 1 may be provided with a pressurization control unit 143*a* instead of the pressurization control unit 143. The light receiving element receives the electromagnetic waves emitted from the light source and reflected off the head of the user 91. The light receiving element outputs a signal indicating the intensity of the received light. The pressurization control unit 143*a* controls the pressure applied by the pressurization unit 15 to the user 91 on the basis of the acceleration signal output by the accelerometer 13 and the signal output by the light receiving element.

For example, the pressurization control unit 143*a* estimates the body fluid volume in the cranium on the basis of the intensity of electromagnetic waves received by the light receiving element. The body fluid volume estimated by the pressurization control unit 143*a* is estimated by an estimation method based on the following physical phenomenon. That is, since electromagnetic waves such as infrared rays emitted from the light source are absorbed by the body fluid in the cranium, the intensity of the electromagnetic waves received by the light receiving element is subject to a phenomenon in which there is the more body fluid in the cranium, the weaker the intensity becomes.

Further, the method of estimating the body fluid volume by the G tolerance improvement device 1 may be an estimation method employing not only electromagnetic waves but also ultrasonic waves. In the estimation method using ultrasound, the diameter of a blood vessel in the neck or head, blood flow, pressure, the size of the sinus and cerebrospinal fluid space, and the like may be measured by ultrasound, and the body fluid volume of the head measured on the basis of the measurement data. Specifically, a body fluid volume estimation method using ultrasonic waves may be a method represented by ultrasonic echo sounding. For example, the method may be one that estimates the body fluid volume on the basis of a reflection point in the body, or a temporal change in the depth or distance, or one that estimates the body fluid volume on the basis of a flow velocity or pressure differential due to a Doppler echo.

In the above-described embodiment, the case where the pressurization control unit 143 acquires the estimated body fluid volume and the estimated change amount is illustrated. However, the pressurization control unit 143 does not necessarily need to estimate the body fluid volume in the cranium and the change amount per unit time, and may estimate only one of them. Further, the pressurization control unit 143 need not necessarily control the pressurization unit 15 on the basis of the body fluid volume in the cranium and the change amount per unit time, and may control the pressurization unit 15 on the basis of only either one.

Furthermore, the present invention is not limited to a special high G environment such as an aircraft, but can be used for avoiding dizziness and fainting associated with a decrease in blood volume in the head. The present invention can also be used for patients with reduced G tolerance, which gives rise to fainting attacks caused by relatively minor G changes such as standing up and ascending in an elevator, which is seen in patients with blood pressure regulation dysfunction due to Sphaet-Drager syndrome, diabetic neuropathy, or the like.

The impedance measurement unit 142 and the pressurization control unit 143 in embodiment described above may be realized by a computer. In that case, a program for realizing these functions may be recorded on a computer-readable recording medium, and the program recorded on this recording medium may be read into a computer system and executed. Here, the "computer system" includes an OS and hardware such as peripheral devices. The "computer-readable recording medium" refers to a storage device such as a flexible medium, a magneto-optical disk, a portable medium such as a ROM or a CD-ROM, and a hard disk incorporated in the computer system. Furthermore, the "computer-readable recording medium" may include one that dynamically holds a program for a short time, such as a communication line in the case where a program is transmitted via a network such as the Internet or a communication line such as a telephone circuit, or one that holds a program for a predetermined time like a volatile memory in a computer system serving as a server or a client in that case. The program may be configured to realize some of the above-mentioned functions, may be configured to realize the above-mentioned functions by combination with a program recorded in advance in a computer system, and may be realized using a programmable logic device such as a field programmable gate array (FPGA) or the like.

The impedance measurement unit 142 and the pressurization control unit 143 are examples of an estimation unit.

The embodiment of the present invention has been described in detail with reference to the drawings. However, the specific configurations are not limited to this embodiment, and designs or the like within a scope not departing from the gist of the present invention are also included.

INDUSTRIAL APPLICABILITY

It is possible to appropriately apply pressure to a user.

REFERENCE SYMBOLS

1: G tolerance improvement device
11: First electrode unit
12: Second electrode unit
13: Accelerometer
14: Control device
15: Pressurization unit
111: First application electrode
112: First measurement electrode
121: Second application electrode
122: Second measurement electrode
141: Application unit
142: Impedance measurement unit
143: Pressurization control unit
91: User
92: Helmet
93: Ear muff

The invention claimed is:

1. A G tolerance improvement device comprising:
an estimator that estimates a body fluid volume in a head of a user and a change amount of the body fluid volume;
a pressurizer adapted to apply pressure to the user based on the body fluid volume and the change amount estimated by the estimator;
a first electrode adapted to make contact with the head of the user; and
a second electrode adapted to make contact with the head or a neck of the user at a location different from the location where the first electrode is adapted to make contact,
wherein the first electrode comprises a first application electrode and a first measurement electrode,
a part of the first measurement electrode is located on a curve, the curve connecting a center point of the first application electrode, which is adapted to make contact with the head, and a center point of the second electrode, which is adapted to make contact with the head or the neck, and being parallel to a surface of the head,
a voltage is applied between the first application electrode and the second electrode,
the estimator estimates the body fluid volume in a cranium of the user and the change amount of the body fluid volume in the cranium per unit time, based on impedance of the head between the first electrode and the second electrode, and
the pressurizer is adapted to apply the pressure to the neck of the user based on the estimated body fluid volume in the cranium and the estimated change amount of the body fluid volume in the cranium per unit time.

2. The G tolerance improvement device according to claim 1, wherein either one or both of the first electrode and the second electrode comprise two or more electrodes.

3. The G tolerance improvement device according to claim 1, wherein the head with which the first electrode is adapted to make contact is either one or both of a crown or temple region of the head of the user.

4. The G tolerance improvement device according to claim 1, wherein the location that the second electrode adapted to make contact with is any one or all of the head, neck, chest, abdomen, waist, and buttocks of the user.

5. The G tolerance improvement device according to claim 1, wherein the change amount is a venous return.

6. The G tolerance improvement device according to claim 1, wherein
the pressurizer is adapted to apply pressure to the user when the body fluid volume is equal to or less than a first threshold value.

7. The G tolerance improvement device according to claim 6, wherein
the pressurizer is adapted to apply pressure to the user when the change amount, indicating a decrease amount or an increase amount of the body fluid volume per unit time, exceeds a second threshold even when the body fluid volume is greater than the first threshold value.

8. The G tolerance improvement device according to claim 1, wherein
the pressurizer is adapted to apply pressure to the user when the change amount exceeds a second threshold value.

9. The G tolerance improvement device according to claim 1, wherein the pressurizer is further adapted to apply the pressure to any of armpits, lower limbs, abdomen, waist, chest, and upper limbs of the user.

10. The G tolerance improvement device according to claim 1, wherein the pressurizer reduces a pressurization amount when the period of applying pressure reaches a predetermined period.

11. The G tolerance improvement device according to claim 1, wherein the pressurizer reduces a pressurization amount when the body fluid volume is equal to or greater than a third threshold value.

12. The G tolerance improvement device according to claim 1, further comprising:
an accelerometer that measures acceleration applied to the user,
wherein the estimator estimates the body fluid volume and the change amount when the acceleration is greater than a fourth threshold value.

13. The G tolerance improvement device according to claim 1, further comprising:
a voltage source that applies the voltage between the first application electrode and the second electrode.

14. The G tolerance improvement device according to claim 1, wherein
the pressurizer is further adapted to apply the pressure when the estimated body fluid volume is equal to or less than a first threshold value, and to apply the pressure when the estimated change amount, indicating a decrease amount or an increase amount of the body fluid volume per unit time, exceeds a second threshold value and the estimated body fluid volume is less than a third threshold value indicating a limit amount of the body fluid volume, even when the estimated body fluid volume is greater than the first threshold value.

15. A control method for a G tolerance improvement device, the G tolerance improvement device including a first electrode adapted to make contact with a head of a user and a second electrode adapted to make contact with the head or a neck of the user at a location different from the location where the first electrode is adapted to make contact, the control method comprising:

applying a voltage between a first application electrode and the second electrode, the first electrode comprising the first application electrode and a first measurement electrode, a part of the first measurement electrode being located on a curve, the curve connecting a center point of the first application electrode, which is adapted to make contact with the head, and a center point of the second electrode, which is adapted to make contact with the head or the neck, and being parallel to a surface of the head;

estimating a body fluid volume in a cranium of the user and a change amount of the body fluid volume in the cranium per unit time, based on impedance of the head between the first electrode and the second electrode; and applying pressure to the neck of the user based on the estimated body fluid volume in the cranium and the estimated change amount of the body fluid volume in the cranium per unit time.

* * * * *